(12) United States Patent
Takekoshi et al.

(10) Patent No.: US 7,490,986 B2
(45) Date of Patent: Feb. 17, 2009

(54) RADIATION IMAGE PROJECTION APPARATUS AND RADIATION IMAGE PROJECTION METHOD

(75) Inventors: Koji Takekoshi, Yokohama (JP); Yuichi Nishii, Tokyo (JP); Hideto Shiozawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/029,964

(22) Filed: Feb. 12, 2008

(65) Prior Publication Data
US 2008/0198968 A1    Aug. 21, 2008

(30) Foreign Application Priority Data
Feb. 15, 2007   (JP)   ............................. 2007-035046

(51) Int. Cl.
*A61B 6/08* (2006.01)
(52) U.S. Cl. ...................................... 378/206; 378/205

(58) Field of Classification Search ................ 378/206, 378/205
See application file for complete search history.

(56) References Cited

U.S. PATENT DOCUMENTS 6,435,717 B1 * 8/2002 Kohler et al. ............... 378/206
7,198,404 B2 * 4/2007 Navab et al. ................ 378/206

FOREIGN PATENT DOCUMENTS

| JP | 3066944 A | 3/1991 |
| JP | 5-064081 A | 3/1993 |
| JP | 2003-275198 A | 9/2003 |
| JP | 2004-073354 A | 3/2004 |

* cited by examiner

*Primary Examiner*—Hoon Song
(74) *Attorney, Agent, or Firm*—Canon USA, Inc., IP Division

(57) ABSTRACT

A radiation image projection apparatus includes an image acquisition unit for acquiring a radiation image obtained by capturing an image of radiation transmitted through an object and a projection unit for projecting the radiation image as visible light onto the object.

10 Claims, 14 Drawing Sheets

RADIATION IMAGE PROJECTION APPARATUS AND RADIATION IMAGE PROJECTION METHOD

BACKGROUND OF THE INVENTION

1. Field of the Invention

The present invention relates to an apparatus that is configured to project a radiation image and a method for the same.

2. Description of the Related Art

Conventionally, film screen systems that combine an intensifying screen and a radiographic film are commonly used as X-ray imaging apparatus in medical facilities. According to this method, X-rays pass through an object, and an intensifying screen converts the X-rays into visible light corresponding to X-ray intensity. Then, radiographic film is exposed to the visible light, thus forming an X-ray image on film.

Physicians perform interpretations by viewing X-ray images formed on the film with a viewing apparatus called a film illuminator (Schaukasten). Furthermore, Japanese Patent Application Laid-Open No. 05-064081 discusses an apparatus that uses an image intensifier, i.e., an image pickup tube that photographs X-rays. The apparatus captures an X-ray image by X-ray radioscopy and displays the X-ray image on a cathode ray tube (CRT) monitor.

Japanese Patent No. 3,066,944 discusses a high-resolution solid X-ray detector that uses a flat panel detector (FPD), i.e., an X-ray detector in a flat-surface form. An object is placed between an X-ray source and an X-ray sensor, and the solid X-ray detector converts X-rays that pass through the object into electrical signals. The X-ray image of the object is converted into electrical signals and captured as digital data. Furthermore, Japanese Patent Application Laid-Open No. 2004-073354 discusses an apparatus that performs X-ray imaging by using a cassette-type portable sensor.

When performing medical procedures such as surgery on a human body at the location of medical treatment, it is sometimes necessary to ascertain an internal structure of the body, especially structures of internal hard tissue and soft tissue. For example, it is necessary to ascertain internal structures during diagnostic imaging of a temporomandibular joint, i.e., a jaw joint, in which a contrast medium is injected into an articular cavity of the temporomandibular joint, and an X-ray image is used for diagnosis. During diagnostic imaging of a temporomandibular joint, a contrast medium is injected by puncturing the skin surface of a patient with a puncture needle. Accurate puncturing with the puncture needle and delivery of the contrast medium to the intended articular cavity are important for performing proper imaging and treatment.

However, puncturing too deep may risk middle cranial fossa damage or penetration through the mandibular fossa capsule to the base of the brain. Due to the complexities regarding articular cavity puncture as described above, a surgeon is required to have extensive anatomical knowledge, experience, and skill.

Furthermore, it is necessary to as certain an internal body structure in other various surgeries as well. Japanese Patent Application Laid-Open No. 2003-275198 discusses a method of ascertaining an internal body structure by projecting an X-ray image onto a half mirror and forming a synthesized image of an object image and the X-ray image on the half mirror.

Japanese Patent Application Laid-Open No. 2003-275198 discusses an apparatus wherein it is necessary to prepare an X-ray image in advance and set the X-ray image into the apparatus. A physician is required to look away from the object to view a half mirror to confirm a synthesized image of an object image and an X-ray image, which makes the operation complex.

SUMMARY OF THE INVENTION

The present invention is directed to an apparatus that makes it easier to ascertain an internal structure of an X-ray imaging object.

According to an aspect of the present invention, a radiation image projection apparatus includes an image acquisition unit configured to acquire a radiation image obtained by capturing an image of radiation transmitted through an object, and a projection unit configured to project the radiation image as visible light onto the object.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DETAILED DESCRIPTION OF THE EMBODIMENTS

Various exemplary embodiments, features, and aspects of the invention will be described in detail below with reference to the drawings.

Figure 1:
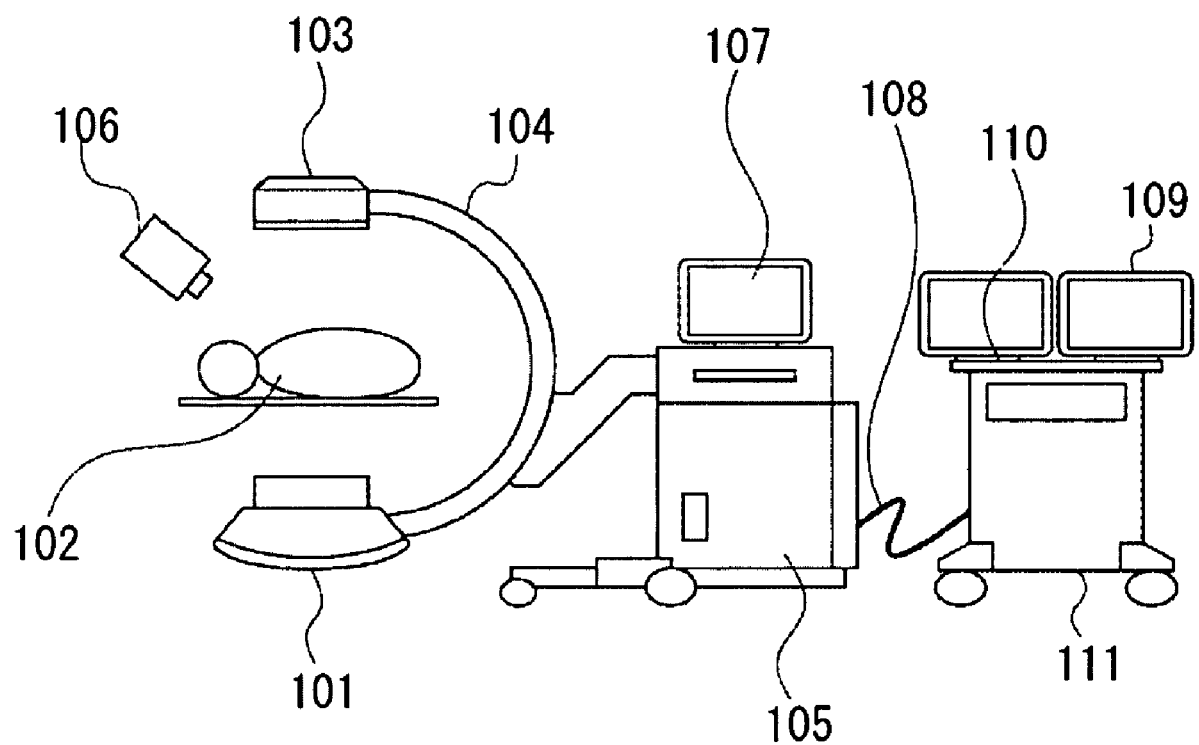
FIG. 1 illustrates an X-ray image projection apparatus according to a first exemplary embodiment of the present invention.

FIG. 1 illustrates an X-ray image projection apparatus of a first exemplary embodiment of the present invention. An X-ray image projection apparatus using X-rays is described in the present embodiment, but applications can also be applied to a radiation image projection apparatus that projects radiation images using a wider range of radiation wavelengths.

An X-ray generating unit 101 emits X-rays in performing radiography. The X-ray generating unit 101 includes metals such as tungsten and molybdenum and applies high electrical voltage to the metal to emit X-rays. However, the X-ray generating unit 101 could also function as a radiation generating unit for generating a wider range of radiation wavelengths.

An object 102 is irradiated with X-rays emitted by the X-ray generating unit 101. The object 102 is typically a patient being photographed with X-rays.

An X-ray sensor 103 that functions as an X-ray image acquisition unit includes an X-ray sensor. The X-ray sensor 103 receives X-rays that pass through the object 102 and creates image signals that represent an X-ray image. An X-ray sensor includes a fluorescent material or silicon material and produces an electrical signal corresponding to the X-ray irradiation amount when irradiated with X-rays.

A C-arm 104 has a C-like shape as illustrated in FIG. 1 and functions as a support structure to maintain the relative positions of the X-ray generating unit 101 and the X-ray sensor 103. When the C-arm 104 moves, the X-ray sensor 103 and the X-ray generating unit 101 are moved relative to the object 102, which enables X-ray imaging of the object 102 from diverse directions.

The X-ray generating unit 101 and the X-ray sensor 103 function as an X-ray imaging unit for capturing X-ray images. Hereinafter, "X-ray imaging unit" refers to the X-ray generating unit 101 and the X-ray sensor 103.

A C-arm cart 105 includes transfer mechanisms such as rollers, and functions as a transfer unit that enables transport of the X-ray imaging unit. In the present embodiment, the X-ray imaging unit is movable by means of the C-arm cart 105, but the X-ray imaging unit may be in a fixed position in the radiography room.

A projection apparatus 106 that functions as a projection unit includes a projector, etc., that projects visible light. The projection apparatus 106 projects visible light onto the object 102.

An arm operation unit 107 includes a monitor such as a cathode ray tube (CRT) monitor or a liquid crystal display (LCD), and input devices such as a keyboard and mouse. The arm operation unit 107 causes the C-arm 104 to make movement and controls the X-ray imaging of the X-ray imaging unit. The radiography operator inputs, via the input devices of the arm operation unit 107, control instructions in order to control the C-arm 104 and the X-ray imaging unit. The control instructions thus input are sent to the X-ray imaging unit. The control status of the X-ray imaging unit is displayed on the monitor of the arm operation unit 107, and the radiography operator can sequentially confirm the control status of the X-ray imaging unit. A keyboard, a mouse, and the like are used as input devices in the exemplary embodiment. However, more general devices such as dedicated membrane buttons, joysticks, an irradiation button, and foot pedals may also be used.

The cable 108 is configured to send the X-ray images captured by the X-ray imaging unit.

A display unit 109 includes a monitor such as a CRT monitor or liquid crystal display, and displays the X-ray image sent through the cable 108.

A display operation unit 110 includes an input device such as a keyboard or a mouse and components necessary for a computer such as a central processing unit (CPU) and random access memory (RAM). The radiography operator inputs the image processing instruction into the input device of the display operation unit 110 in order to perform image processing of the X-ray image sent through the cable 108. The image processing refers to, for example, stitch processing that combines a plurality of X-ray images, or density correction processing that corrects the density of the X-ray image. The RAM of the display operation unit 110 stores an image processing program for image processing. The CPU of the display operation unit 110 reads the image processing program stored in RAM and performs image processing on the X-ray image according to the image processing program. The X-ray image that is subjected to the image processing is then displayed on the display unit 109 or projected from the projection apparatus 106.

A monitor cart 111 includes transfer mechanisms such as rollers, and functions a transfer unit hat enables transport of the display operation unit 110 and the display unit 109.

Figure 2:
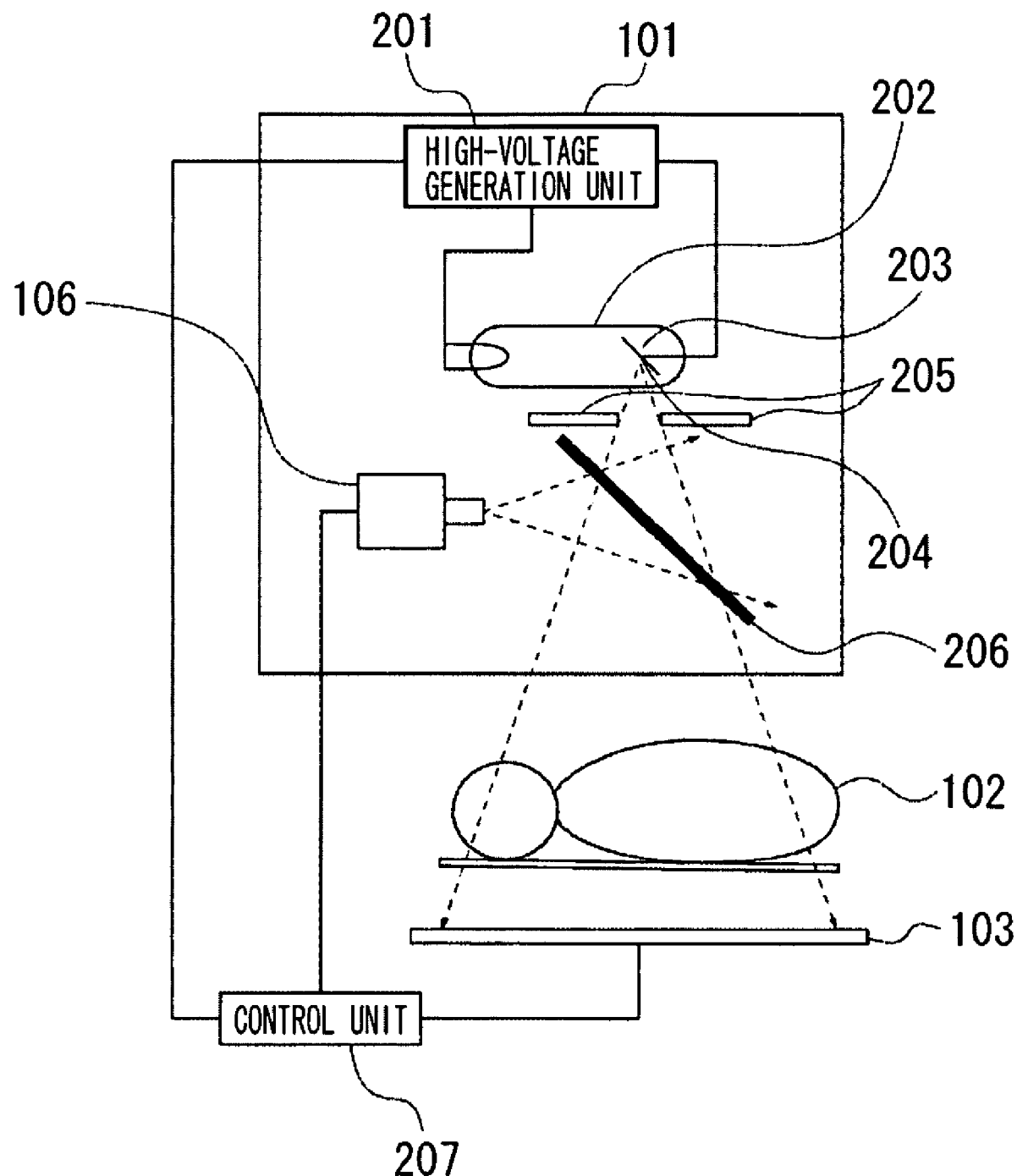
FIG. 2 illustrates a detailed configuration around the X-ray imaging unit according to the first exemplary embodiment of the present invention.

FIG. 2 illustrates a detailed configuration around the X-ray imaging unit including the X-ray generating unit 101 and the X-ray sensor 103.

A high-voltage generation unit 201 is mounted on the X-ray generating unit 101 and produces high electrical voltage between approximately 25 kV and 150 kV to emit X-rays.

An X-ray tube 202 includes a glass vacuum tube, receives the voltage from the high-voltage generation unit 201, and emits X-rays.

A target 203 is contained in the X-ray tube 202 and includes a metal such as tungsten or molybdenum. The voltage from the high-voltage generation unit 201 creates an electrical potential inside the X-ray tube 202, and a flow of electrons is produced inside the X-ray tube 202. The flowing electrons impact the target 203, and a part of the energy of the impacted electrons is emitted from the target 203 as X-rays.

An X-ray focal point 204 is the location in the target 203 where X-rays are created owing to the impacting electrons. A collimator 205 includes a metal such as lead that does not transmit X-rays. The collimator 205 partially blocks the X-rays emitted from the X-ray focal point 204. By partially blocking X-rays, the collimator 205 serves as an aperture that adjusts the X-rays to be irradiated on the object 102.

A half mirror 206 is a reflective mirror that transmits X-rays and reflects visible light. By arranging the half mirror 206 at a position illustrated in FIG. 2, X-rays radiating from the X-ray focal point 204 are transmitted through the half mirror 206, and the visible light projected from the projection apparatus 106 is reflected from the half mirror 206. Thus, the object 102 is irradiated with two sources.

By using the half mirror 206 in the present embodiment, the projection apparatus 106 can be arranged at an optically equivalent position to the X-ray focal point 204.

In general language, a first capture position and a second capture position, where light of the same wavelength can be captured, are referred to as optically equivalent positions. In the present embodiment, "optically equivalent positions" is also defined as positions where the same projection occurs for a first projecting position and a second projecting position, i.e., the projection at a first projecting position and the projection at a second projecting position become the same. The half mirror 206 is arranged at the position as illustrated in FIG. 2 in the present embodiment so that the projection can be performed same as the case where the projection apparatus 106 is arranged at the position of the X-ray focal point 204.

A control unit 207 includes a CPU and RAM, and controls the X-ray imaging unit and the projection apparatus 106 according to control an instruction from the arm operation unit 107, etc. Information stored in the RAM includes a control program for controlling the voltage produced by the high-voltage generation unit 201, a setting program that sets the image that is created by visible light projected from the projection apparatus 106, and a control program that controls movement of the C-arm 104. The CPU reads the control program and the setting program from the RAM and controls the X-ray imaging unit and the projection apparatus 106 according to the programs.

Specifics of the control method of the control unit 207 are described below.

Figure 3:
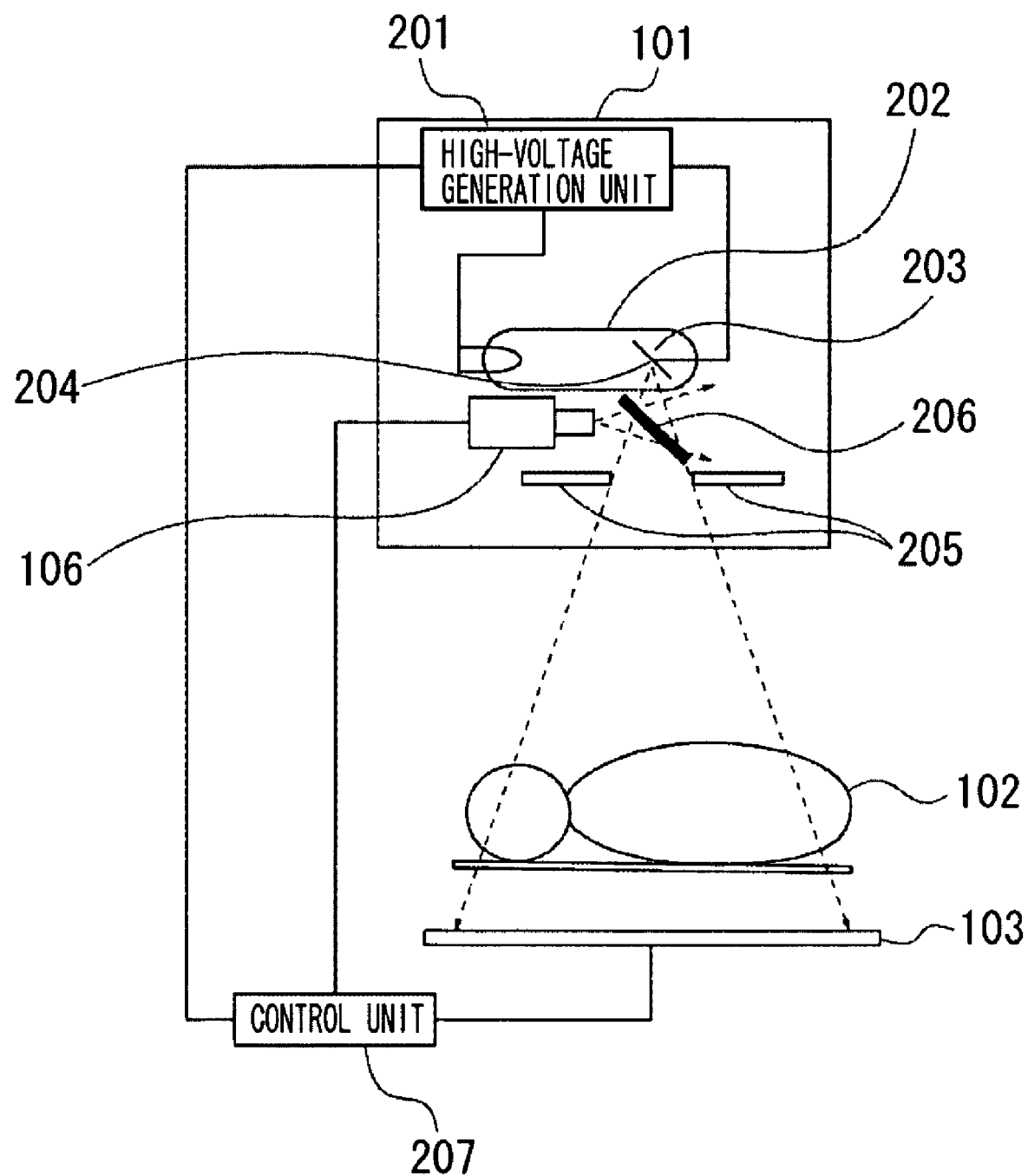
FIG. 3 illustrates a detailed configuration around the X-ray imaging unit according to the first exemplary embodiment of the present invention.

FIG. 3 illustrates a detailed configuration around an X-ray imaging unit, similar to FIG. 2. The components of FIG. 3 are similar to FIG. 2, but the projection apparatus 106 is mounted on the X-ray generating unit 101. Since the projection apparatus 106 is arranged within the X-ray generating unit 101, an apparatus configuration can be simplified.

Figure 4:
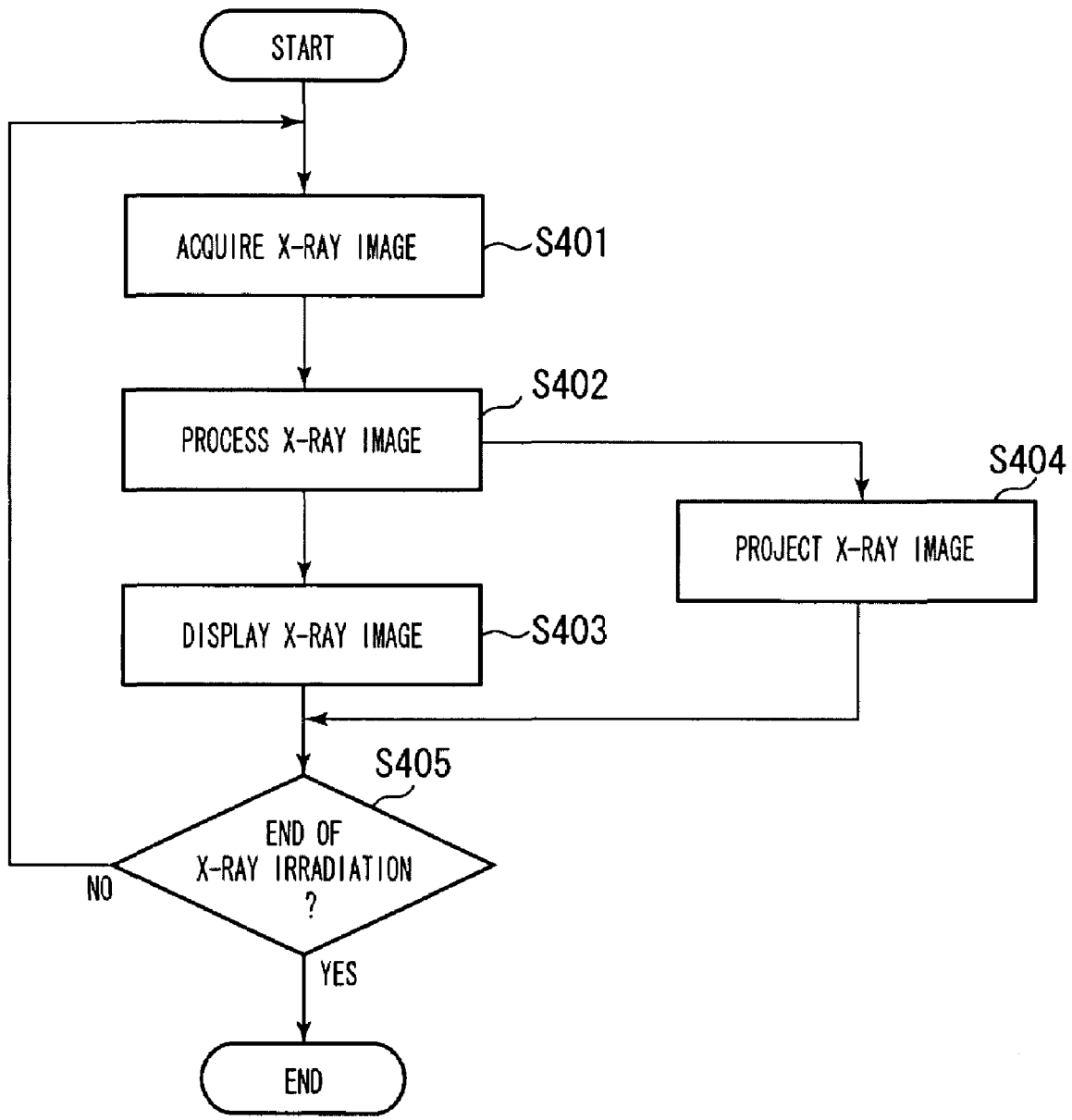
FIG. 4 illustrates a process flow according to the first exemplary embodiment of the present invention.

FIG. 4 illustrates a process flow of the X-ray image projection apparatus according to the present embodiment. The process flow of FIG. 4 proceeds while the components of FIG. 1 and FIG. 2 function under control of the control unit 207.

In step S401, the control unit 207 controls the X-ray generating unit 101 and the X-ray sensor 103 according to the control instructions from the arm operation unit 107, and thereby executes the X-ray imaging. In the present embodiment, the control unit 207 performs X-ray imaging according to the control instruction from the arm operation unit 107, but X-ray imaging may be performed automatically according to a program stored in the control unit 207. As described above, the X-ray sensor 103 captures the X-ray image by detecting X-rays that pass through the object 102.

In step S402, the display operation unit 110 performs image processing on the X-ray image captured at step S401. At the image processing step, density correction processing, stitch processing, etc. are performed as described above. Because a processed X-ray image is subsequently projected by the projection apparatus 106, image processing appropriate for projection may also be performed. For example, level transformation processing, color processing that converts a black-and-white X-ray image to a red-green-blue (RGB) image, black-and-white inversion processing, gamma correction processing, and high-luminance processing can be performed.

In step S403, the display operation unit 110 displays the image processed by the display unit 109 at step S402. For example, a physician can observe the displayed image and perform a diagnosis.

In step S404, the control unit 207 projects the X-ray image processed in step S402 by the projection apparatus 106. The projection apparatus 106 is arranged in an optically equivalent position to the X-ray focal point 204 as described above, and therefore the same projection is performed as projection from the X-ray focal point 204. By projecting the X-ray projection image as visible light from the projection apparatus 106 arranged in an optically equivalent position to the X-ray focal point 204, an X-ray image appears on the surface of the object 102.

The X-ray image that appears on the surface of the object 102 is recognizable by the naked eye of a human. Therefore, because the projection apparatus 106 is arranged in an optically equivalent position to the X-ray focal point 204, the X-ray image appears on the surface of the object 102 as if the observer is seeing the internal structure of the object 102.

Accordingly, a physician can easily ascertain an internal structure of an object merely by observing a surface of the object 102.

In step S405, the control unit 207 determines whether the X-ray generating unit 101 ends emitting of X-rays. The control unit 207 ends the operation of the X-ray image projection apparatus when a pre-set end time comes, or a radiography operator inputs an end instruction (YES in step S405). In the case where the process is not ended (NO in step S405), the process returns to step S401 and once again X-ray imaging in step S401 is performed.

Thus, a physician can easily ascertain an internal structure of an object without using a complex apparatus by performing the process as described above. Further, the process as described above allows the physician to ascertain the internal structure of the object while observing the object, which prevents complexity of the physician's operation.

In a general X-ray imaging apparatuses, when X-rays are emitted, the X-ray imaging apparatus also functions as a visual light irradiation unit that irradiates the object with visible light together with the X-rays from the X-ray generating unit 101. The irradiation area of the visible light changes according to an aperture of the X-ray generating unit 101 and the like. Irradiation of visible light is performed to enable the physician and the radiography operator to easily ascertain the emission of X-rays. However, in the present embodiment, when projecting the X-ray image onto the object 102, the projected image and the visible light emitted from the X-ray generating unit 101 are superimposed, which can result in a decrease in the visibility of both the projected image and the irradiating visible light. In order to compensate for this, according to the present embodiment, in a case where both the projected image and the visible light are applied, an irradiation amount of at least one of the projected image and the visible light is reduced so that visibility of both the projected image and the irradiating visible light can be improved. The reduction amount of the irradiation may be pre-set, or the amount may be appropriately changed according to an instruction from the physician or the radiography operator.

In the first exemplary embodiment, the positions of the X-ray generating unit 101, the X-ray sensor 103, and the projection apparatus 106 are fixed relative to each other. However, body movement of the object 102 or positional deviation between the X-ray generating unit 101 and the X-ray sensor 103 may cause displacement of the positions of the X-ray image projected from the projection apparatus 106 and the object 102.

A second exemplary embodiment of the present invention provides an X-ray image projection apparatus that addresses this.

Figure 5:
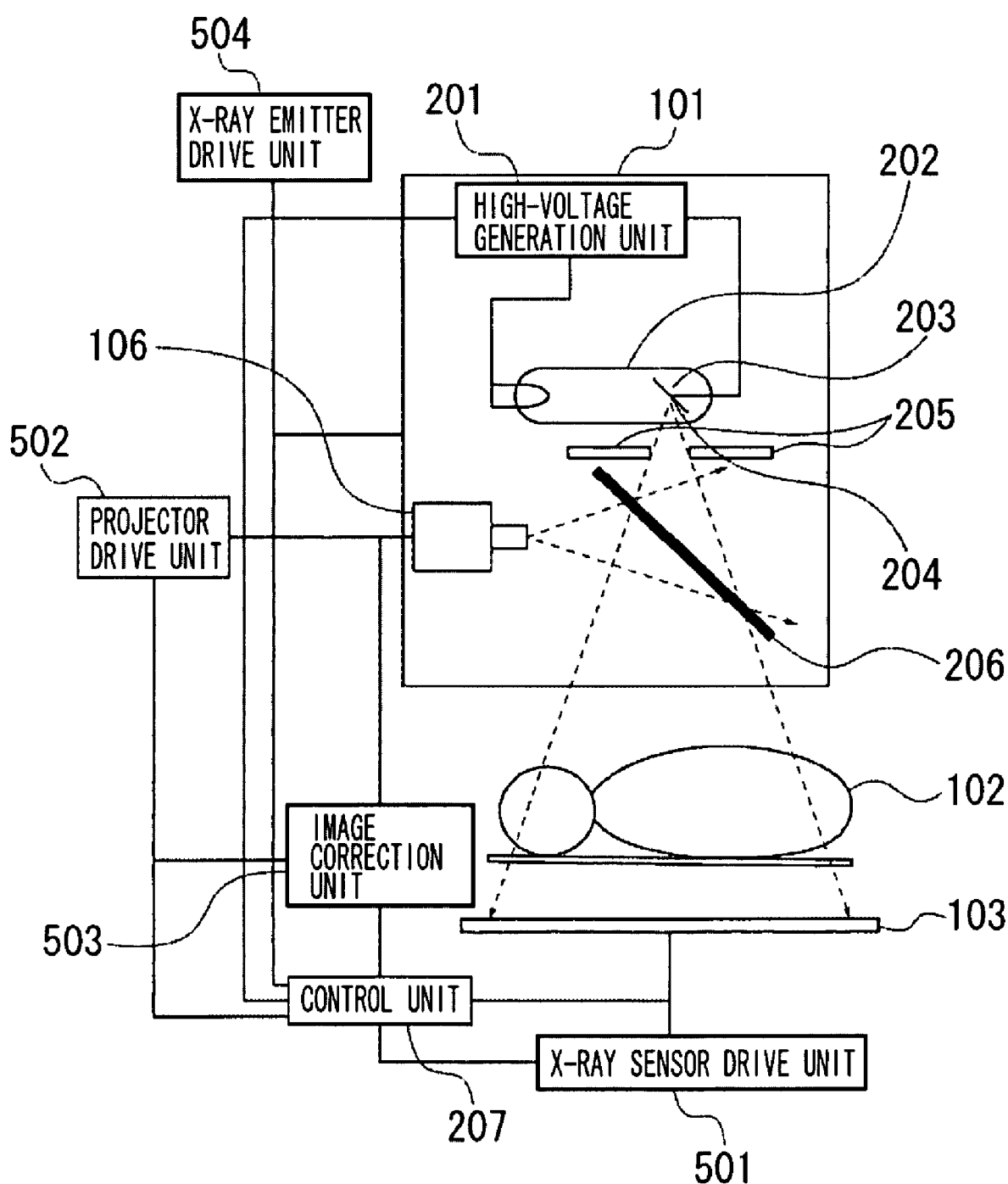
FIG. 5 illustrates a detailed configuration around the X-ray imaging unit according to a second exemplary embodiment of the present invention.

FIG. 5 illustrates a detailed configuration around an X-ray imaging unit of an X-ray image projection apparatus according to the second exemplary embodiment. As illustrated in FIG. 5, the configuration is similar to that of the X-ray imaging unit illustrated in FIG. 2. As such, only the differences between the configuration of FIG. 5 and FIG. 2 will be described below.

An X-ray sensor drive unit 501 includes a drive mechanism such as a motor and drives an X-ray sensor 103.

A projector drive unit 502 includes a drive mechanism such as a motor and drives a projection apparatus 106.

An image correction unit 503 includes devices such as a CPU and a RAM, and performs processes such as rotation and horizontal movement on an image projected by the projection apparatus 106.

An X-ray emitter drive unit 504 includes a drive mechanism such as a motor and drives an X-ray generating unit 101.

The X-ray sensor drive unit 501, the projector drive unit 502, the image correction unit 503, and the X-ray emitter drive unit 504 each function according to an instruction from the arm operation unit 107 or the display operation unit 110.

Figure 6:
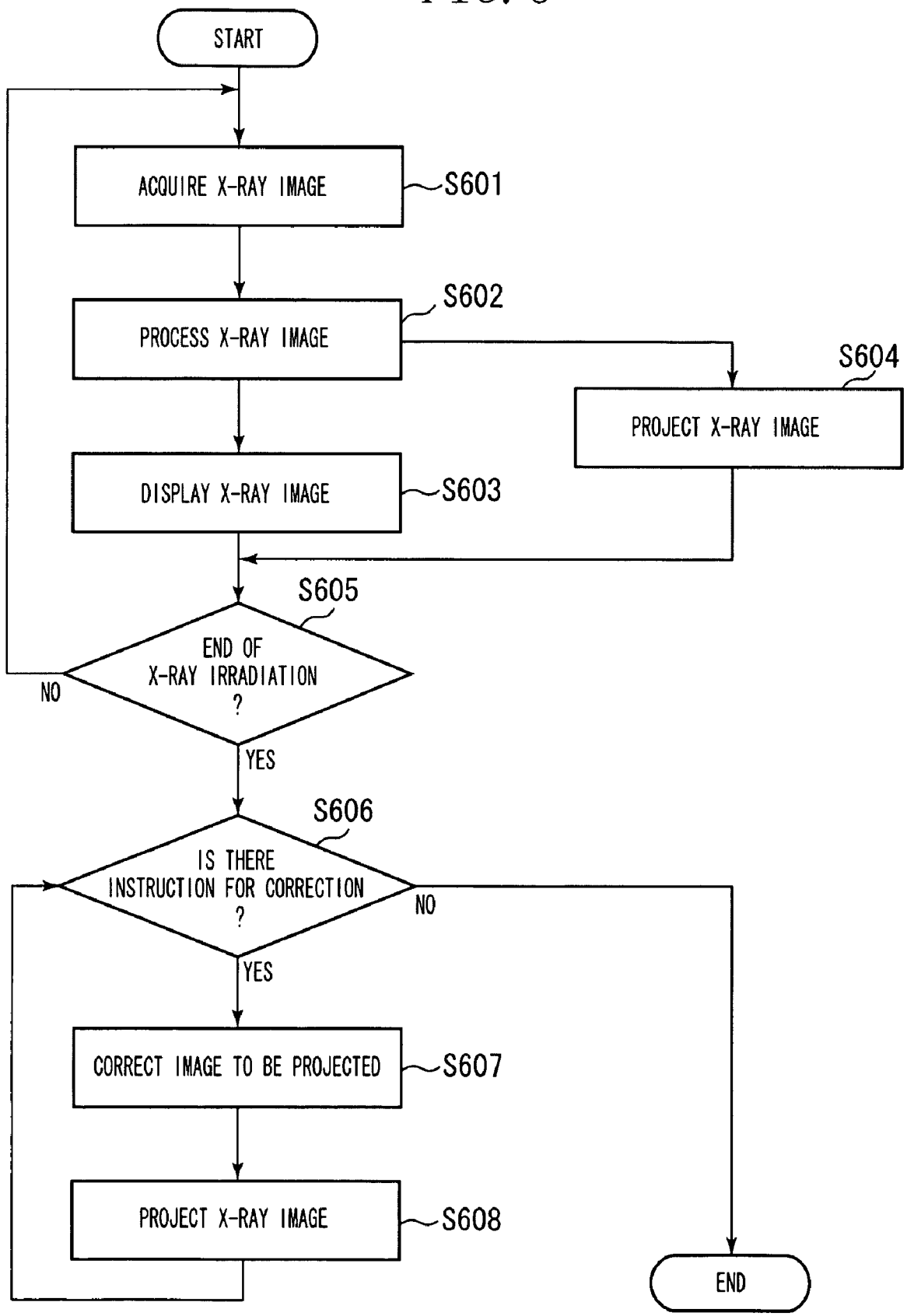
FIG. 6 illustrates a process flow of correction processing of a projected X-ray image according to the second exemplary embodiment of the present invention.

FIG. 6 illustrates a process flow for correcting an X-ray projection image according to the present embodiment.

The process of FIG. 6 proceeds when the components of FIG. 1 and FIG. 5 function under control of the control unit 207 and the image correction unit 503.

The process from step S601 through step S605 is similar to the process of step S401 through step S405 of FIG. 4, and thus a detailed description is omitted herein.

In the case where X-ray irradiation ends (YES in step S605), the process proceeds to step S606.

In step S606, the control unit 207 receives a correction instruction from a radiography operator. The radiography operator inputs the instruction from the display operation unit 110. As described above, a positional deviation may occur between the object 102 and the projected X-ray image. In the case where a positional deviation is identified, a correction instruction for correcting the positional deviation is entered (YES in step S606). In the case where there is no correction instruction for correcting the positional deviation, (NO in step S606), the process ends.

In step S607, the image correction unit 503 performs correction of the projected X-ray image according to the instruction input in step S606.

More particularly, the image correction unit 503 performs image processing to the X-ray image, and corrects the X-ray image to become a rotated or horizontally moved image. There are various correction methods that can be used, such as moving the pixels of the X-ray image in a prescribed direction. Any method that would enable the practice of the present invention is applicable.

In step S608, the projection apparatus 106 projects the X-ray image similar, as previously described. The projected X-ray image is an image subjected to the correction in step S607, so that the X-ray image is projected onto the object 102 without positional deviation. After the projection of the X-ray image is made, the process returns to step S606, and the control unit 207 determines whether to perform further correction of the X-ray image.

Figure 7:
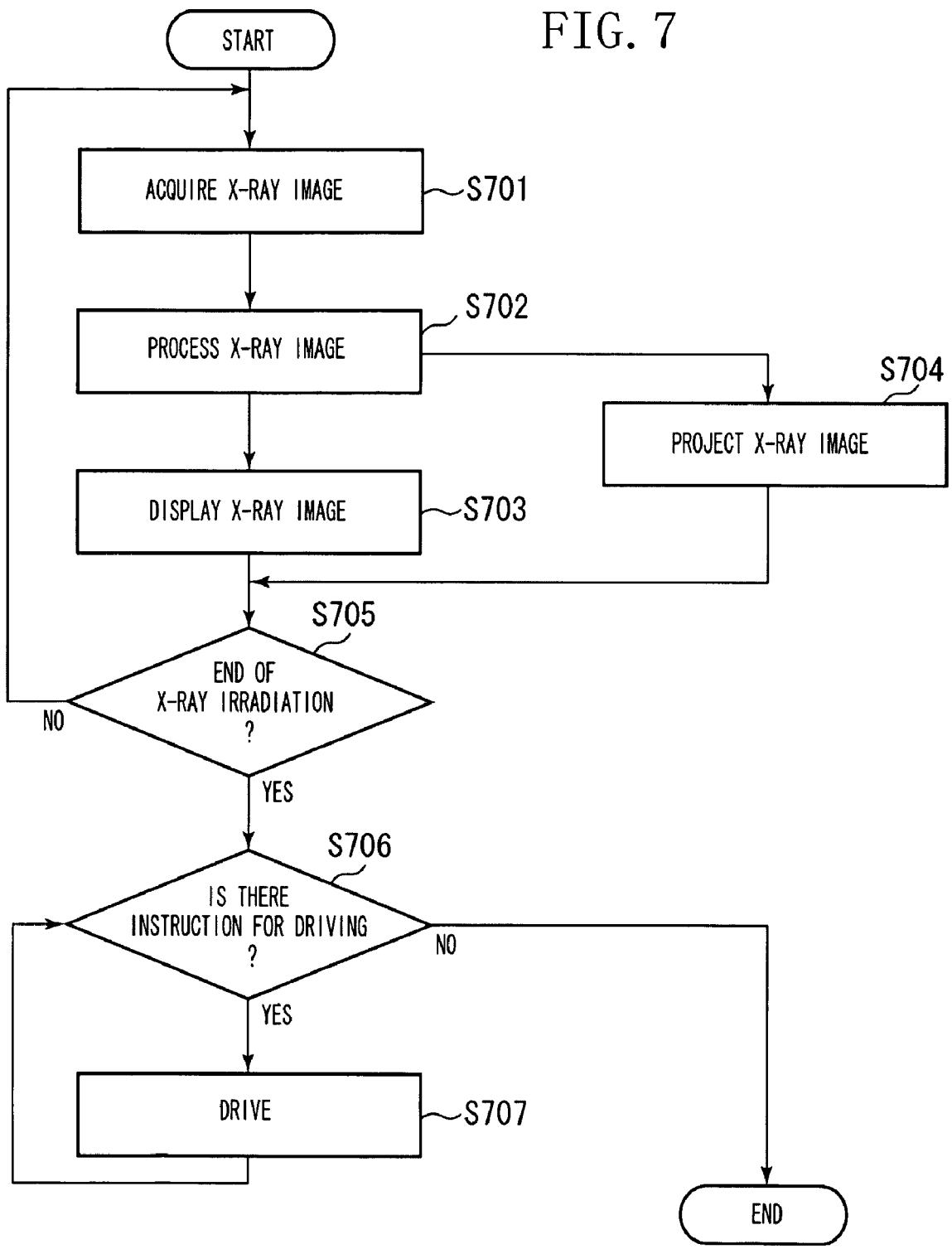
FIG. 7 illustrates a process flow of drive processing according to the second exemplary embodiment of the present invention.

FIG. 7 illustrates a flow of drive processing for driving any of the X-ray sensor drive unit 501, the projector drive unit 502, and/or the X-ray emitter drive unit 504 according to the present embodiment.

The process from step S701 through step S705 is similar to the process of step S401 through step S405 of FIG. 4, and thus a detailed description is omitted herein.

When X-ray irradiation ends (YES in step S705), the process proceeds to step S706.

In step S706, the control unit 207 receives a drive instruction from the radiography operator. The radiography operator inputs the instruction from the arm operation unit 107. As described above, positional deviation may occur between the object 102 and the projected X-ray image. In the case where a positional deviation is identified, a drive instruction for correcting the positional deviation is inputted (YES in step S706). The drive instruction includes an instruction for selecting what to drive, i.e., selecting any of the X-ray sensor drive unit 501, the projector drive unit 502, and/or the X-ray emitter drive unit 504. If there is no drive instruction for correcting positional deviation (NO in step S706), the process ends.

In step S707, any of the X-ray sensor drive unit 501, the projector drive unit 502, and/or the X-ray emitter drive unit 504 is driven according to the drive instructions input in step S706. More particularly, any of the X-ray sensor drive unit 501, the projector drive unit 502, and/or the X-ray emitter drive unit 504 is driven horizontally or driven rotationally. One or more of the X-ray sensor drive unit 501, the projector drive unit 502, and/or the X-ray emitter drive unit 504 may be driven.

In the present embodiment, the correction processing of the positional deviation is performed according to the instruction of the radiography operator, but the control unit 207 may perform the correction processing without the instruction of the radiography operator.

Thus, by performing the process flow in FIG. 6 or FIG. 7 as described above, the positional deviation between the object 102 and the projected X-ray image can be corrected.

In the present embodiment, in order to correct the positional deviation between the object 102 and the projected X-ray image, horizontal movement and rotation of the apparatus of step S707 are performed. However, only rotation may be performed in the case where the positional deviation is known in advance to be minute.

Figure 8:
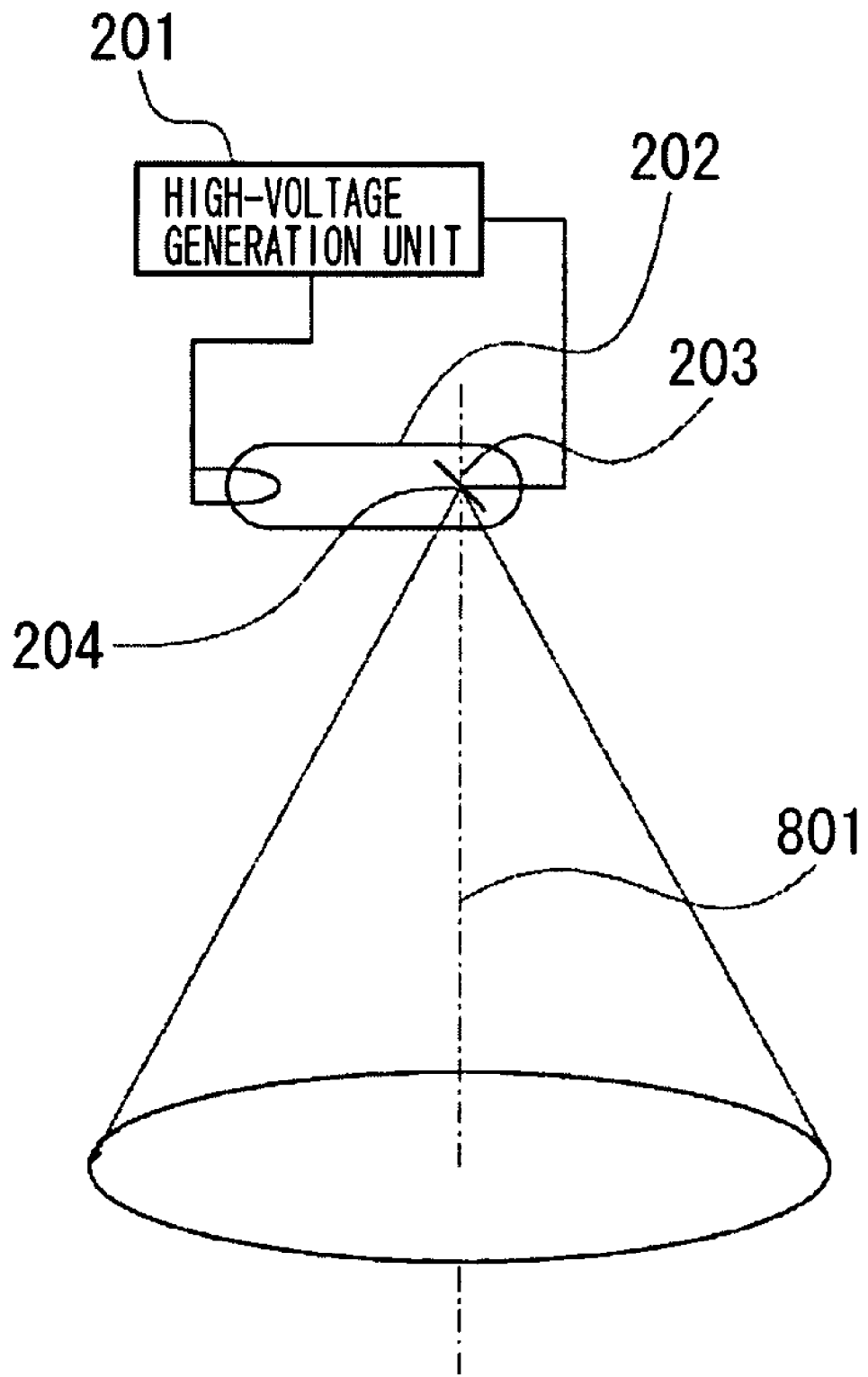
FIG. 8 illustrates X-rays emitted by an X-ray generating unit.

FIG. 8 illustrates X-rays generated in the X-ray generating unit 101. As illustrated in FIG. 8, the area irradiated with the X-rays takes a conic shape. When rotation is performed for the correction, the conic shape of FIG. 8 is calculated in advance. If rotation is performed around an X-ray axis 801 at the center of the conic shape, then correction precision can be improved. Also in a case where the rotation is performed to correct the projected image in step S607, the correction precision can be improved by similarly performing correction processing based on the X-ray axis 801 at the center of the conic shape.

Figure 9:
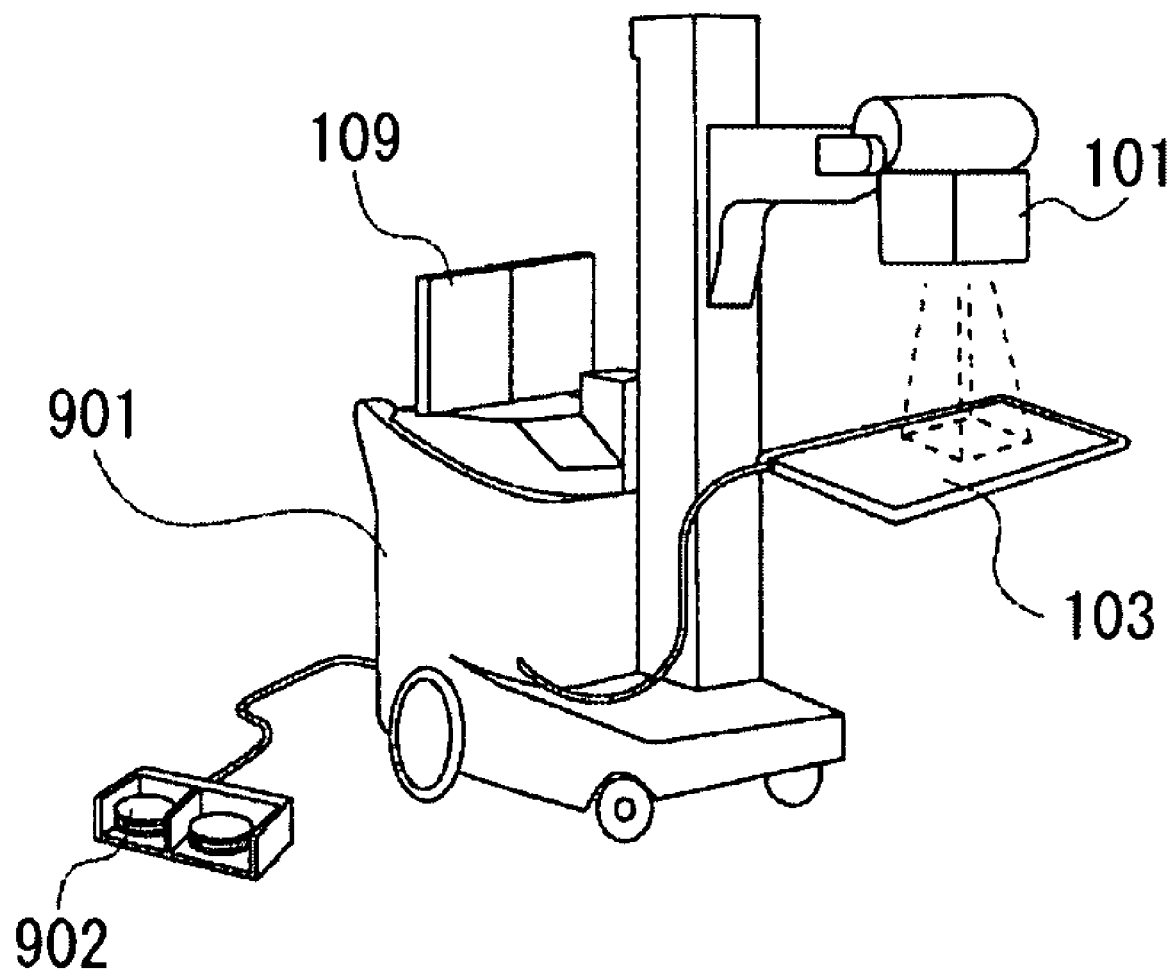
FIG. 9 illustrates an X-ray image projection apparatus according to a third exemplary embodiment of the present invention.

FIG. 9 is an external view of an X-ray image projection apparatus according to a third exemplary embodiment of the present invention. The X-ray image projection apparatus of FIG. 9 provides improved portability.

The X-ray image projection apparatus of FIG. 9 includes an X-ray generating unit 101, an X-ray sensor 103, and a display unit 109 similar to the X-ray image projection apparatus of the first exemplary embodiment. As illustrated in FIG. 9, the X-ray sensor 103 is movable.

A portable examination cart 901 is a transfer unit for moving the X-ray imaging apparatus.

A foot pedal 902 is an instruction apparatus that controls X-ray imaging and improves portability.

The configuration of FIG. 1 may be added to the X-ray image projection apparatus of the present embodiment if necessary.

Figure 10:
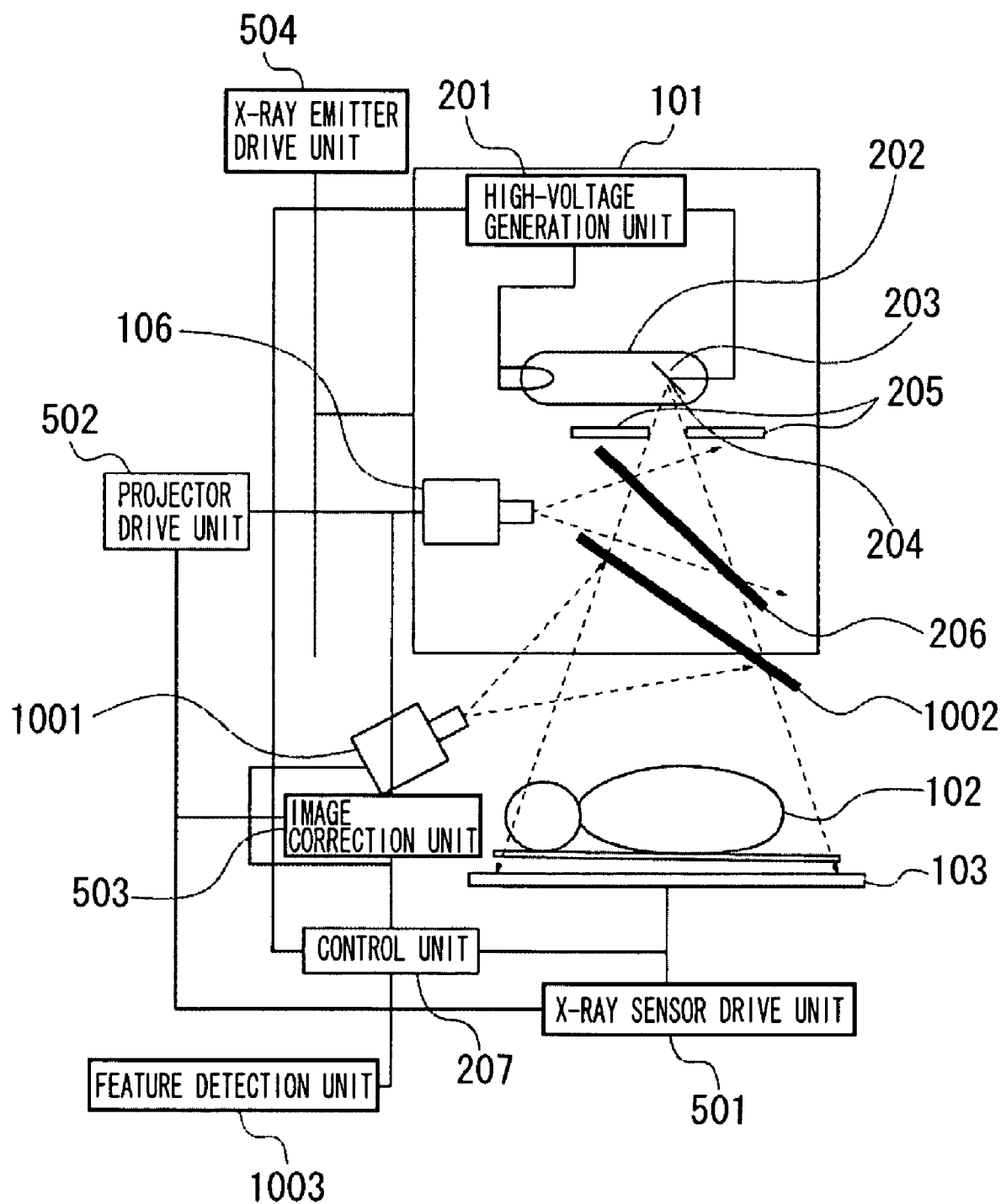
FIG. 10 illustrates a detailed configuration around an X-ray imaging unit according to the third exemplary embodiment of the present invention.

FIG. 10 illustrates a detailed configuration around the X-ray imaging unit according to the present embodiment. The configuration illustrated in FIG. 10 is similar to the configuration illustrated in FIG. 5. As such, only the differences between the two configurations will be described below.

A television camera 1001 is a visible light imaging apparatus including a general video camera, etc. that records an object 102 and captures a visible light image of the object 102.

A half mirror 1002 is a reflective mirror that transmits 50 percent of the visible light and reflects the remaining 50 percent. Because 50 percent of the visible light is reflected, the television camera 1001 can record the object 102 with reflected light from the half mirror 1002. Also, because 50 percent of the visible light is transmitted, the projected visible light from the projection apparatus 106 passes through the half mirror 1002 and is applied to the object 102.

A feature detection unit 1003 functions as a position acquisition unit and detects feature portions of the visible light image acquired from the television camera 1001, or of the X-ray image captured by the X-ray sensor 103. A feature portion refers to a unique region in the image. By detecting the feature portion, an image position, etc. can be detected. For example, the feature portion is a portion having a unique shape, color, etc. By recording the position of the feature portion in advance, the position of the feature portion in the image can be calculated.

Various methods exist that can be used as a detection method of feature portions. Any detection that would enable practice of the present invention is applicable. For example, in the case where the feature portion is a unique shape, first, binary processing is performed on an acquired image. Then, it is determined whether a region within the binary-processed image matches the pre-recorded unique shape. In the case where there is a match with the unique shape, the matching area is determined to be the feature portion.

Figure 11:
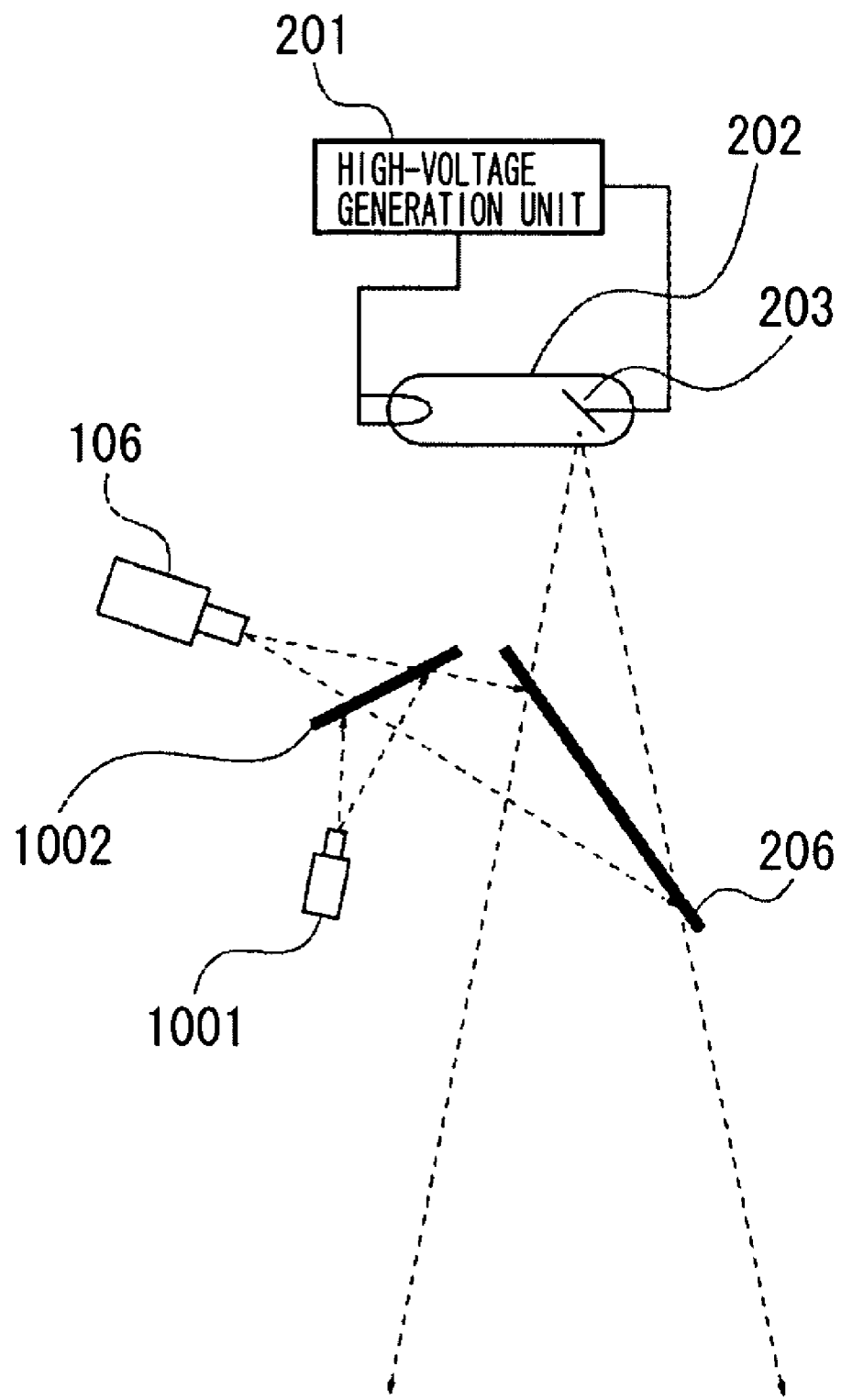
FIG. 11 illustrates an exemplary variation wherein the arrangement of a television camera and a half mirror is altered according to the third exemplary embodiment of the present invention.

FIG. 11 illustrates the television camera 1001 and the half mirror 1002 of the present embodiment in a different arrangement. As illustrated in FIG. 11, the visible light reflected from the half mirror 206 is further reflected from the half mirror 1002, and thus the television camera 1001 can acquire visible light from the object 102. Furthermore, the X-ray image projection apparatus of the present embodiment can function even in the case where the positions of the television camera 1001 and the projection apparatus 106 are reversed.

Figure 12:
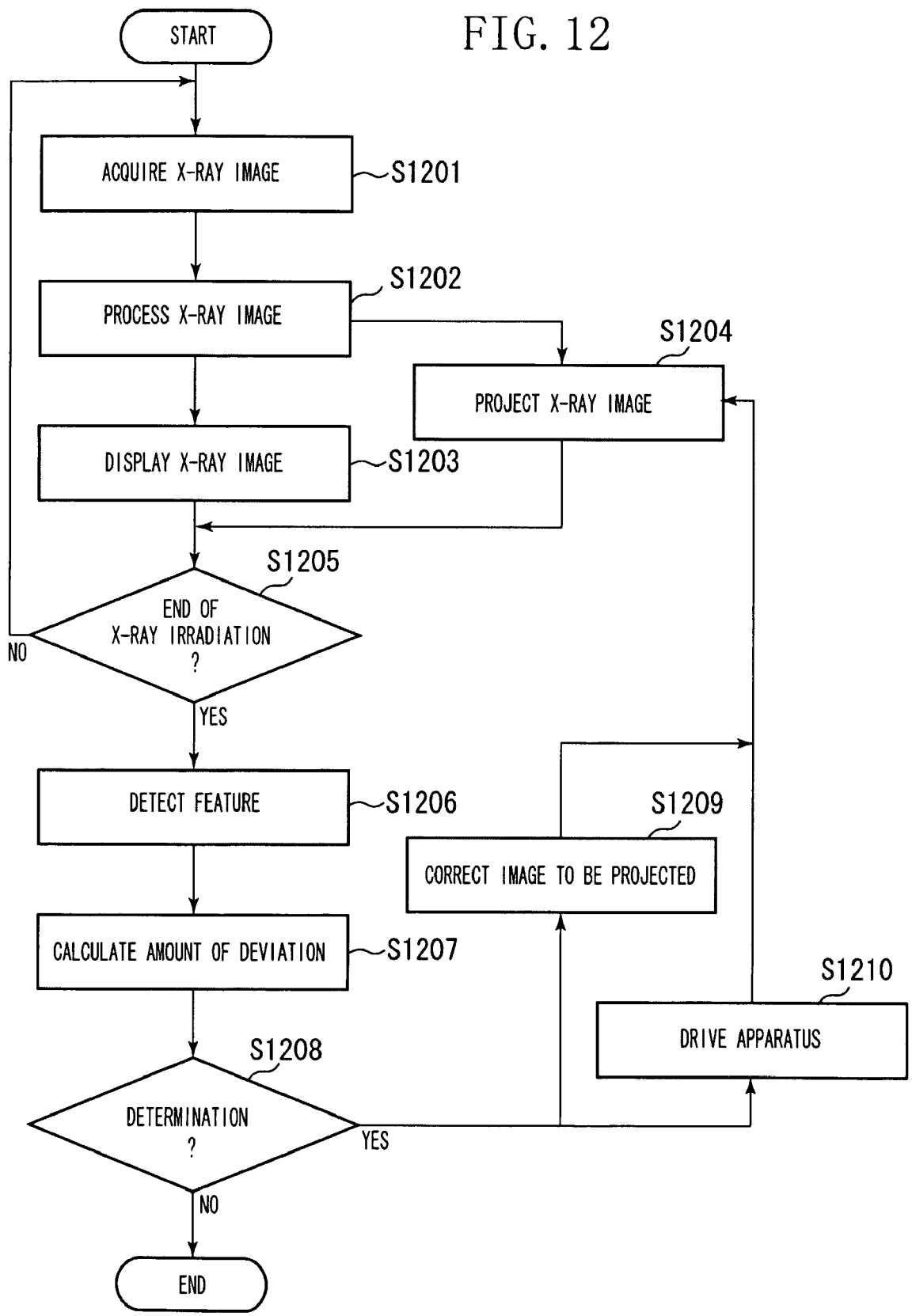
FIG. 12 illustrates a process flow according to the third exemplary embodiment of the present invention.

FIG. 12 illustrates a process flow of the present embodiment. Under control of the control unit 207, the image correction unit 503, and the feature detection unit 1003, the function of each of the components in FIG. 10 can be performed according to the process of FIG. 12.

The process of step S1201 through step S1205 is similar to the processing of step S401 through step S405 in FIG. 4, and thus a detailed description is omitted herein.

After the X-ray irradiation ends (YES in step S1205), the process proceeds to step S1206.

In step S1206, the feature detection unit 1003 detects the feature portion in the X-ray image acquired from the X-ray sensor 103 or in a visible image acquired from the television camera 1001.

Figure 13A:
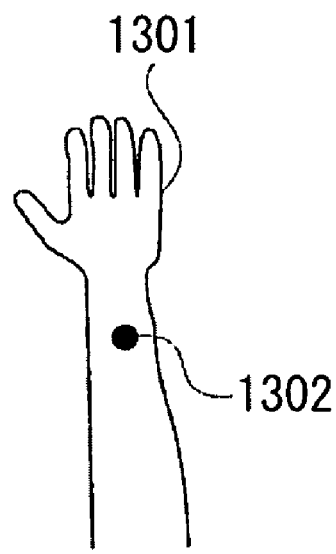
FIGS. 13A through 13D illustrate relationships between an arm of an object and a marker according to the third exemplary embodiment of the present invention.

FIG. 13A illustrates a feature portion in a visible image according to the present embodiment.

An arm 1301 is an arm of the object 102.

A marker 1302 represents a feature portion. The marker 1302 includes a material, such as lead, that does not transmit X-rays. Because the marker 1302 includes lead, the marker 1302 can be detected even while capturing the X-ray image, and therefore the position can be ascertained. Typically, the marker 1302 is a minute substance to avoid disturbing the imaging process.

The position of the marker 1302 can be detected in the visible image of FIG. 13A by performing the detection processing of the feature portion as described above.

Figure 13B:
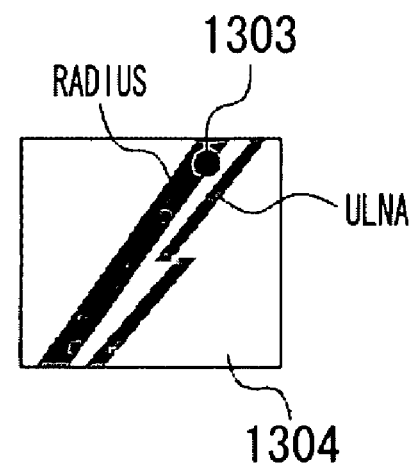

FIG. 13B illustrates an X-ray image according to the present embodiment.

An X-ray image 1304 is an image detected by the X-ray sensor 103. The images of a radius and an ulna inside the arm 1301 of an object are captured.

An image marker 1303 is a marker 1302 captured while capturing the X-ray image. The marker 1302 is also captured in the X-ray image 1304 because the marker 1302 does not transmit X-rays.

In step S1207, a feature detection unit 1003 calculates a deviation amount between the visible image of the arm 1301 of an object and the X-ray image 1304. The following is a description of positional deviation.

Figure 13C:
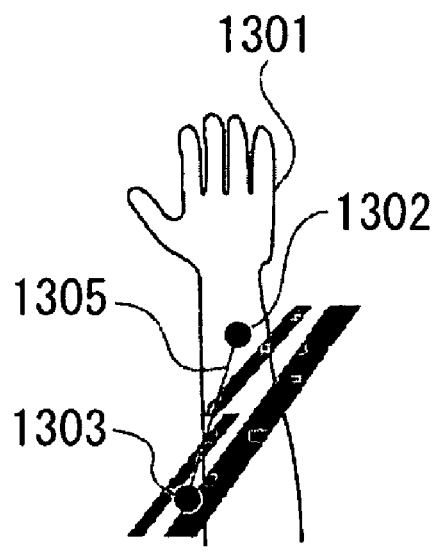

FIG. 13C illustrates a state where the X-ray image 1304 is projected onto the arm 1301 of an object.

A positional deviation 1305 illustrates a deviation of positions of the marker 1302 and the marker 1303. In order to calculate the positional deviation 1305, first, the feature detection unit 1003 detects a feature portion from the visible image of FIG. 13C acquired from the television camera 1001. The feature portions of FIG. 13C are the marker 1302 and the image marker 1303. The feature detection unit 1003 can calculate the positional deviation 1305 by detecting the marker 1302 and the image marker 1303, and by performing a difference operation.

In step S1208, the control unit 207 determines whether to drive any of the X-ray generating unit 101, the X-ray sensor 103, and/or the projection apparatus 106, or to correct the image. The control unit 207 performs the determination by acquiring an instruction from the radiography operator, and by performing the determination based on the acquired instruction. For example, the radiography operator observes the positional deviation 1305 and gives an instruction to drive the projection apparatus 106 to correct the positional deviation 1305. The control unit 207 may also determine whether the positional deviation 1305 is larger than a pre-set threshold, and determine whether to perform apparatus driving or image correction.

In the case where it is determined to correct the image in step S1208, the process proceeds to step S1209. In the case where it is determined to perform apparatus driving in step S1208, the process proceeds to step S1210. When the image correction and the apparatus driving are determined not to be performed (NO in step S1208), the process ends.

In step S1209, the image correction unit 503 performs correction processing of the projected image based on the determination of step S1208. The specific process is similar to the projected image correction processing in step S607 of FIG. 6. When the process ends, the process returns to step S1204, and the control unit 207 once again performs X-ray image projection.

In step S1210, based on the determination of step S1208, the control unit 207 performs driving of the apparatus. The specific process is similar to the driving in step S707 of FIG. 7. When the process ends, the process returns to step S1204, and the control unit 207 once again performs X-ray image projection.

Thus as described above, the positions of the marker 1302 and the image marker 1303 can be aligned by performing the process of step S1209 or step S1210.

Figure 13D:
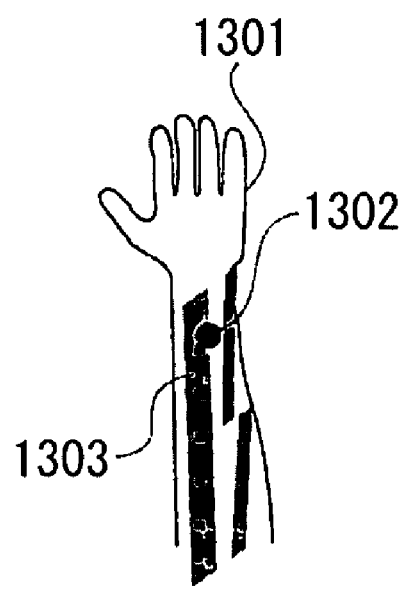

FIG. 13D illustrates a state where the positions of the marker 1302 and the image marker 1303 are aligned. As illustrated in FIG. 13D, if the positions of the marker 1302 and the image marker 1303 are aligned, then the X-ray image 1304 is properly projected onto the arm 1301 of an object. Therefore, by performing the processes described above, the X-ray image 1304 can be properly projected onto the arm 1301 of an object. One marker is detected as a feature portion in the process flow of FIG. 12, but a plurality of markers can also be detected as feature portions.

FIGS. 14A through 14D illustrate cases where the number of markers is greater than the number of markers in FIGS. 13A through 13D.

Figure 14A:
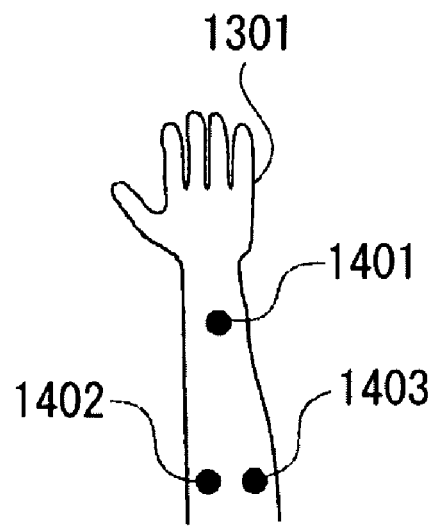
FIGS. 14A through 14D illustrate arrangement of a plurality of markers according to the third exemplary embodiment of the present invention.

FIG. 14A illustrates the arm 1301 of an object and markers. As illustrated in FIG. 14A, a plurality of markers is arranged. A marker 1401, a marker 1402, and a marker 1403 have similar shapes, but are arranged in different positions.

Figure 14B:
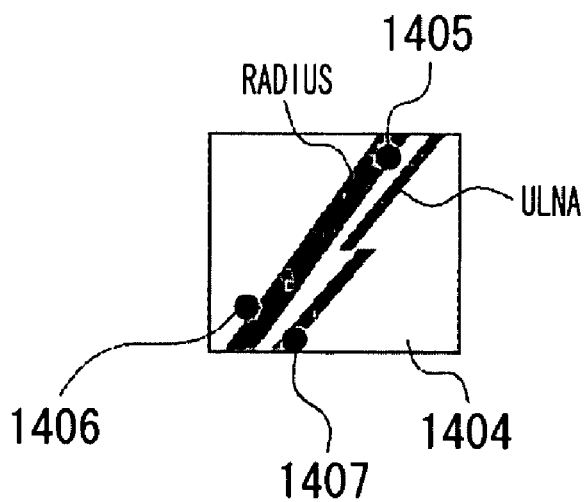

FIG. 14B illustrates an X-ray image showing an increased number of markers.

An X-ray image 1404 shows an image marker 1405, an image marker 1406, and an image marker 1407 that respectively correspond to the marker 1401, the marker 1402, and the marker 1403.

Figure 14C:
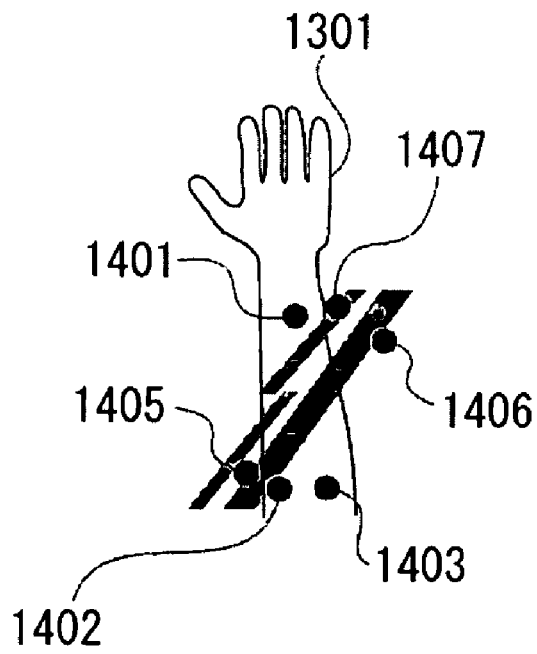

FIG. 14C illustrates a state where an X-ray image 1404 is projected onto the arm 1301 of an object. In FIG. 14C, a positional deviation occurs between the object 1301 and the X-ray projection image 1404.

Figure 14D:
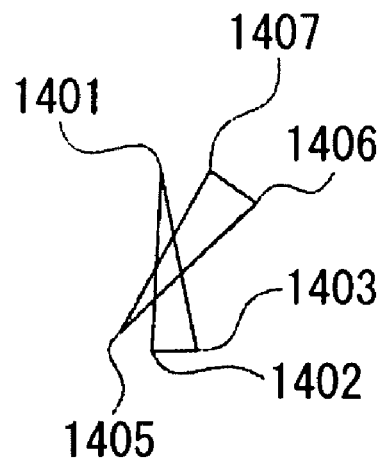

FIG. 14D is an abstracted image of the positional deviation of the markers in FIG. 14C. As illustrated in FIG. 14C, the marker 1401, the marker 1402, and the marker 1403 can form a triangular shape. Further, the image marker 1405, the image marker 1406, and the image marker 1407 can also form a triangular shape. Therefore, the positional deviation of the markers of FIG. 14C can be considered as the deviation of the triangular shapes of FIG. 14D. As illustrated in FIGS. 14A through 14D, in the case where a plurality of markers is arranged, the feature detection unit 1003 can detect the deviation of a polygon, such as a triangle, in step S1208. By using a plurality of markers, the detection precision of the positional deviation can be improved.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2007-035046 filed Feb. 15, 2007, which is hereby incorporated by reference herein in its entirety.

What is claimed is:

1. A radiation image projection apparatus comprising:
   an image acquisition unit configured to acquire a radiation image obtained by capturing an image of radiation transmitted through an object;
   a mirror configured to transmit radiation and reflect visible light; and
   a projection unit configured to project the radiation image as visible light onto the object by reflecting the visible light on the mirror, and by being arranged at a position optically equivalent to the position of a radiation generating unit configured to emit radiation onto the object by using the mirror.

2. The radiation image projection apparatus according to claim 1, further comprising:
   the radiation generating unit; and
   a radiation detection unit configured to detect radiation emitted from the radiation emission unit;
   wherein the image acquisition unit acquires a radiation image from radiation detected by the radiation detection unit.

3. The radiation image projection apparatus according to claim 2, wherein the projection unit is arranged in a position capable of performing a projection similar to a projection performed when the radiation image is projected from the radiation generating unit.

4. The radiation image projection apparatus according to claim 2, further comprising:
   a visual light irradiation unit configured to apply visible light corresponding to the generation of radiation by the radiation generating unit;
   wherein at least one of the projection unit and the visual light irradiation unit limits the irradiation of visible light when the projection unit applies the radiation image as visible light.

5. The radiation image projection apparatus according to claim 2, further comprising:
   a position acquisition unit configured to acquire a position of the object; and
   a drive unit configured to drive at least one of the image acquisition unit, the radiation generating unit, or the radiation detection unit, based on a position of the object.

6. The radiation image projection apparatus according to claim 5, further comprising an image correction unit configured to correct the radiation image projected as visible light onto the object based on the position of the object.

7. The radiation image projection apparatus according to claim 1, further comprising:
   a feature detection unit configured to detect a feature portion of the object;
   wherein the position acquisition unit acquires a position of the object based on the detected feature portion.

8. The radiation image projection apparatus according to claim 7, wherein:
   the feature detection unit detects a plurality of feature portions of the object, and
   wherein the position acquisition unit acquires a position of the object based on shapes formed by the feature portions.

9. A method comprising:
   acquiring a radiation image obtained by capturing an image of radiation transmitted through an object;
   projecting the radiation image as visible light onto the object by reflecting the visible light on a mirror, the mirror being configured to transmit radiation and reflect visible light, with a projection unit configured to project the radiation image as the visible light onto the object; and
   arranging the projection unit at a position optically equivalent to the position of a radiation generating unit configured to emit radiation onto the object by using the mirror.

10. A computer readable medium storing computer-readable instructions, the computer-readable instructions causing a computer to perform a method comprising:
   acquiring a radiation image obtained by capturing an image of radiation transmitted through an object;
   projecting the radiation image as visible light onto the object by reflecting the visible light on a mirror, the mirror being configured to transmit radiation and reflect visible light, with a protection unit configured to project the radiation image as the visible light onto the object; and
   arranging the projection unit at a position optically equivalent to the position of a radiation generating unit configured to emit radiation onto the object by using the mirror.

* * * * *